(12) United States Patent
Yamazaki et al.

(10) Patent No.: US 6,409,141 B1
(45) Date of Patent: Jun. 25, 2002

(54) PARTICLE ANALYZER AND COMPOSITE LENS FORMED BY INTEGRALLY JOINING PLURAL LENS ELEMENTS OF DIFFERENT FOCAL POINTS

(75) Inventors: Masao Yamazaki; Yutaka Nagai; Katsuhiro Tsuchiya; Yoshiyuki Takahara, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/629,425

(22) Filed: Jul. 31, 2000

Related U.S. Application Data

(62) Division of application No. 09/038,281, filed on Mar. 11, 1998, now Pat. No. 6,084,670.

(30) Foreign Application Priority Data

Mar. 11, 1997 (JP) .............................................. 9-072780
May 7, 1997 (JP) .............................................. 9-131653

(51) Int. Cl.[7] .............................................. B29D 11/00
(52) U.S. Cl. ........................ 249/117; 359/721; 359/742; 425/808; 425/470
(58) Field of Search ................................ 425/808, 556; 249/116; 359/742, 720, 721, 724, 743; 362/332

(56) References Cited

U.S. PATENT DOCUMENTS

| 3,004,370 A | * | 10/1961 | Ruhle ........................ 350/437 |
| 4,050,782 A | | 9/1977 | Uchida et al. ................. 350/96 |
| 4,188,121 A | | 2/1980 | Hirleman, Jr. et al. ....... 356/336 |
| 4,341,471 A | | 7/1982 | Hogg et al. .................. 356/343 |
| 4,456,344 A | * | 6/1984 | Bordignon .................... 350/452 |
| 4,775,229 A | | 10/1988 | Ichihara et al. ............... 436/63 |
| 4,904,069 A | * | 2/1990 | Nakata ........................ 350/452 |
| 4,921,205 A | * | 5/1990 | Drew, Jr. et al. .............. 249/61 |
| 5,017,497 A | | 5/1991 | De Grooth et al. ........... 436/63 |
| 5,049,177 A | * | 9/1991 | Nakata ........................... 65/93 |
| 5,390,050 A | * | 2/1995 | Yanagi et al. ................ 359/742 |
| 5,760,871 A | * | 6/1998 | Kosoburd et al. .......... 351/161 |
| 5,958,469 A | * | 9/1999 | Richards ...................... 425/175 |
| 6,046,847 A | * | 4/2000 | Takahashi .................... 359/457 |
| 6,052,226 A | * | 4/2000 | Takahashi .................... 359/457 |
| 6,074,196 A | * | 6/2000 | Shimizu et al. .............. 425/556 |
| 6,157,500 A | * | 12/2000 | Yamazaki et al. ........... 359/741 |

FOREIGN PATENT DOCUMENTS

| EP | 0 696 731 A2 | 2/1996 | .......... G01N/15/14 |
| GB | 2 042 166 A | 9/1980 | .......... G01N/21/53 |
| JP | 57-144502 | 9/1982 | |
| JP | 52-10151 | 7/1983 | |
| JP | 61-41185 | 9/1986 | |
| JP | 60-129705 | 7/1993 | |
| JP | 7-67634 | 7/1995 | |

(List continued on next page.)

*Primary Examiner*—Frank G. Font
*Assistant Examiner*—Layla Lauchman
(74) *Attorney, Agent, or Firm*—Sughrue Mion, PLLC (57) ABSTRACT

A flow cell 2, a composite lens 15, and first to third detectors 16 to 18 are arranged in this sequence in the light pathway of light emitted from a laser light source 1. The composite lens 15 is configured by a convex lens 15a, and lens elements 15b and 15c. These lenses have different focal lengths. When the posture of the composite lens is correct, light impinging on the convex lens forms an image on the first detector. Therefore, the positioning of the composite lens is enabled. When particles in the flow cell are irradiated with laser light, forward scatter is produced. Forward small angle scatter having a small scattering angle impinges on the first lens element 15b to be collected thereby, and is then received by the second detector 17. Forward large angle scatter having a large scattering angle impinges on the second lens element 15c in the outermost periphery to be collected thereby, and is then received by the third detector 18 which is remotest from the composite lens.

8 Claims, 11 Drawing Sheets

FOREIGN PATENT DOCUMENTS

| | | | | |
|---|---|---|---|---|
| JP | 8-271509 | 10/1996 | .......... | G01N/33/49 |
| JP | 8-320404 | 12/1996 | | |
| JP | 2615093 | 3/1997 | | |
| WO | WO 91/03725 | 3/1991 | .......... | G01N/21/00 |

* cited by examiner

PARTICLE ANALYZER AND COMPOSITE LENS FORMED BY INTEGRALLY JOINING PLURAL LENS ELEMENTS OF DIFFERENT FOCAL POINTS

This is a divisional of application Ser. No. 09/038,281 filed Mar. 11, 1998, now U.S. Pat. No. 6,084,670 the disclosure of which is incorporated herein by reference.

BACKGROUND OF THE INVENTION

1. Field of the Invention

The invention relates to a device which can sort particles (sample) such as cells and blood corpuscles on the basis of scattering angle information of scatter.

2. Related Art

Flow cytometers, which is a one of kind of particle analyzer, include a cell sorter, a cell analyzer, and a particle analyzer (blood analyzer) which incorporate these devices. Such a flow cytometer is configured in the following manner. Particles flowing through or dropping from a flow cell are irradiated with light. Forward scatter, orthogonal scatter, or the like which is produced as a result of the irradiation is detected. Particles such as cells and blood corpuscles are sorted on the basis of the detected optical information.

Figure 8:
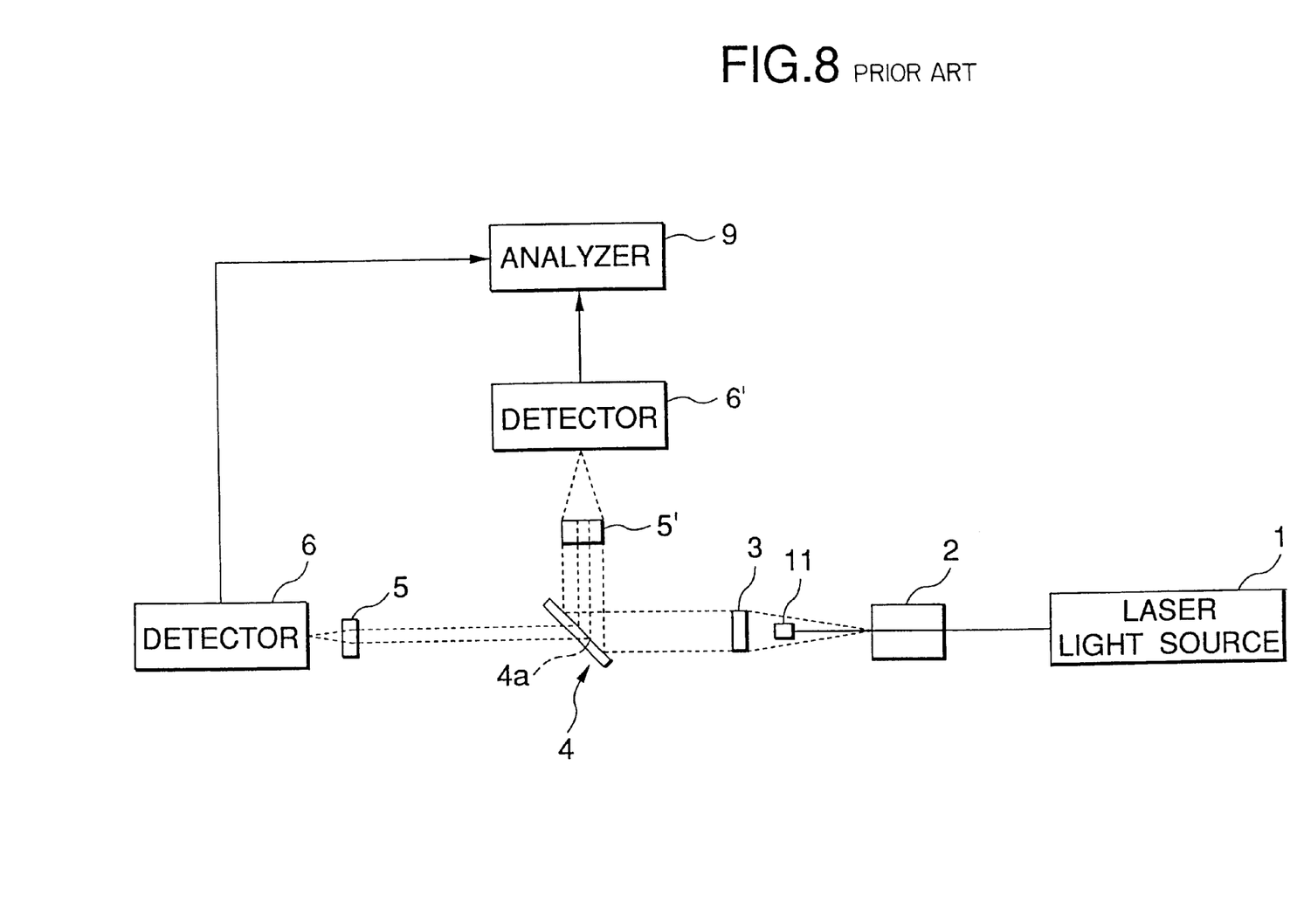
FIG. 8 is a view showing an example of the conventional art.
Figure 9:
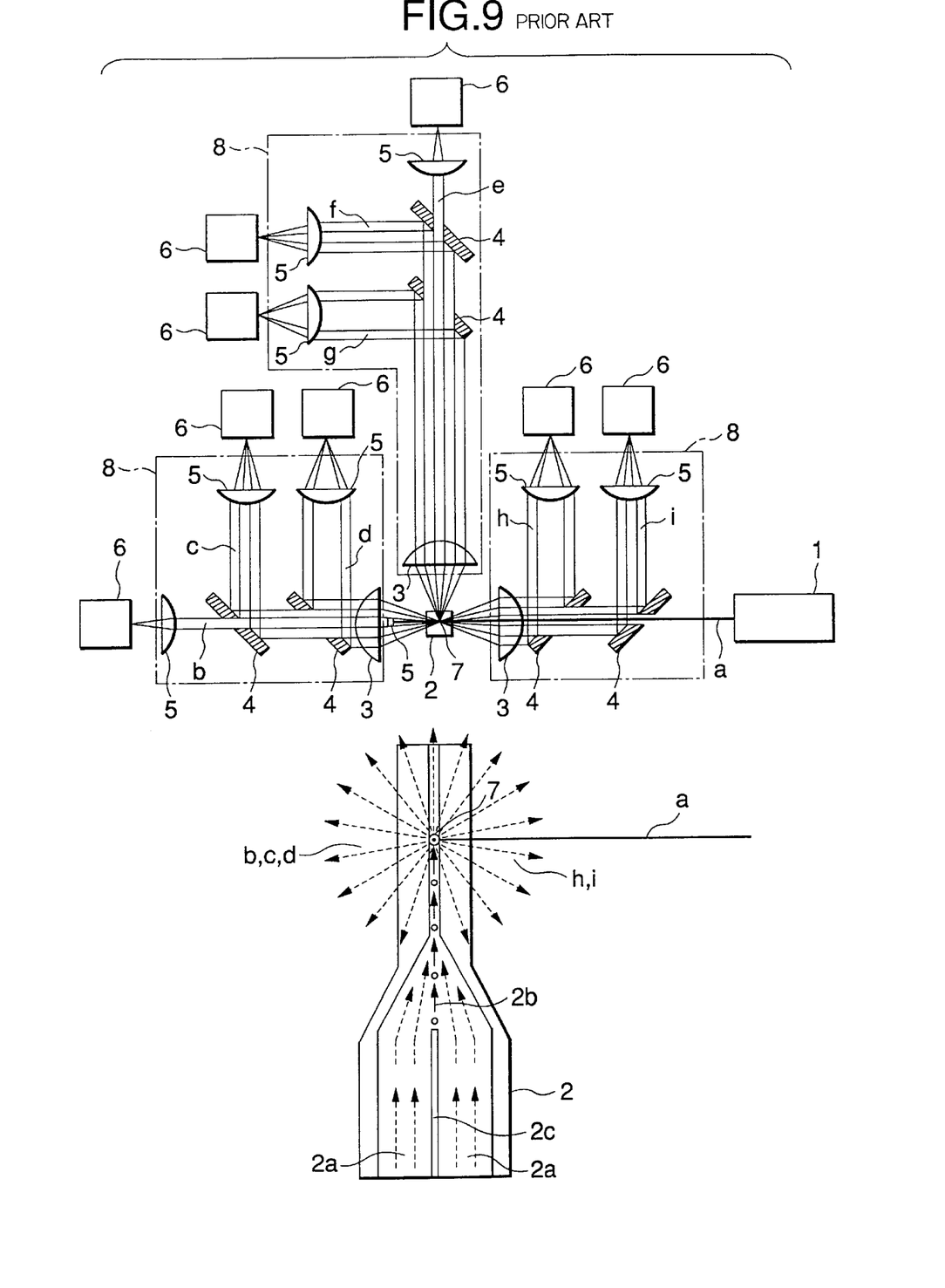
FIG. 9 is a view showing another example of the conventional art.

It is known that, in forward scatter, the scattering angle varies depending on the kind of particles. Therefore, a device is proposed in which forward scatter is collected with being split into plural regions of different scattering angles, and forward scatter of each region is measured, thereby sorting particles. An example of such a device is disclosed in Unexamined Japanese patent publication HEI. 8-271509. In the device, cells contained leukocytes are optically detected so that cells of a small content are accurately sorted. FIGS. 8 and 9 show the configuration for detecting forward scatter in the disclosed device.

As shown in FIG. 9 including a section view of a flow cell used in the flow cytometer, the interior of the flow cell 2 has a structure wherein a sample tube 2c into which the sample (particles) flows is positioned in a center portion of a sheath fluid 2a which flows in a sheath-like manner and a sample flow 2b containing particles are formed in the tip end portion of the tube so as to be surrounded by the sheath fluid, thereby continuously supplying particles to a capillary portion. Since the capillary portion is irradiated with laser light a, a particle 7 passing through the portion function as the scattering source to produce forward scatters b, c, and d, orthogonal scatters e, f, and g (these scatters are directed to the back face of the sheet, and hence not illustrated), and back scatters h and i.

As shown in FIG. 8, the laser light emitted from the light source 1 is transmitted through the flow cell 2 and then blocked by an obscurator 11 which is immovably disposed. The forward scatter b, c, d or the like is converted into a collimated pencil of ray by a collimator lens 3 which is disposed in front of the flow cell 2, and then impinges on a forward-disposed mirror 4. A hole 4a is formed at the center of the mirror 4. Light of a small scattering angle in the forward scatter passes through the hole 4a and is then collected onto a first detector 6 by a first collecting lens 5. Light of a large scattering angle in the forward scatter impinges on the periphery of the mirror 4 to be reflected thereby so that the light pathway is changed by 90 deg., and is then collected onto a second detector 6' by a second collecting lens 5'. Each of the first and second detectors 6 and 6' is configured by a light/voltage converter element such as a photodiode, and converts received light into an electric signal corresponding to the intensity of the light. The signal is supplied to an analyzer 9.

In other words, the first detector 6 detects the intensity of forward small angle scatter having a small scattering angle, and the second detector 6' detects that of forward large angle scatter having a large scattering angle. The analyzer 9 calculates forward small angle scatter data and forward large angle scatter data from the incoming detection signals, and stores the calculated data. The analyzer calculates also 2-dimension coordinate data of the intensities of forward small angle scatter and forward large angle scatter. The analyzer 9 sequentially supplies the calculated forward small angle scatter data and forward large angle scatter data to an external display device (not shown) so that the data are displayed on a screen as a scattergram of a 2-dimension coordinate.

It is known that scatters produced by laser light irradiation have the following directional properties:

when the size of a particle is larger than the wavelength of the laser light, forward scatter is produced;

when the size of a particle is at a similar degree as the wavelength of the laser light, forward and orthogonal scatters are produced; and when the size of a particle is smaller than the wavelength of the laser light, forward, orthogonal, and back scatters are produced.

In order to sort particles more correctly, therefore, an actual device is configured in the following manner. As shown in FIG. 9, for the forward scatters b, c, and d, an optical system 8 having a collimator lens 3, perforated mirrors 4, and collecting lenses 5, and detectors 6 for detecting the intensities of the scatters are disposed; for the orthogonal scatters e, f, and g also, an optical system 8 and detectors 6 are disposed; and, for back scatters h and i also, an optical system 8 and detectors 6 are disposed.

Figure 10A:
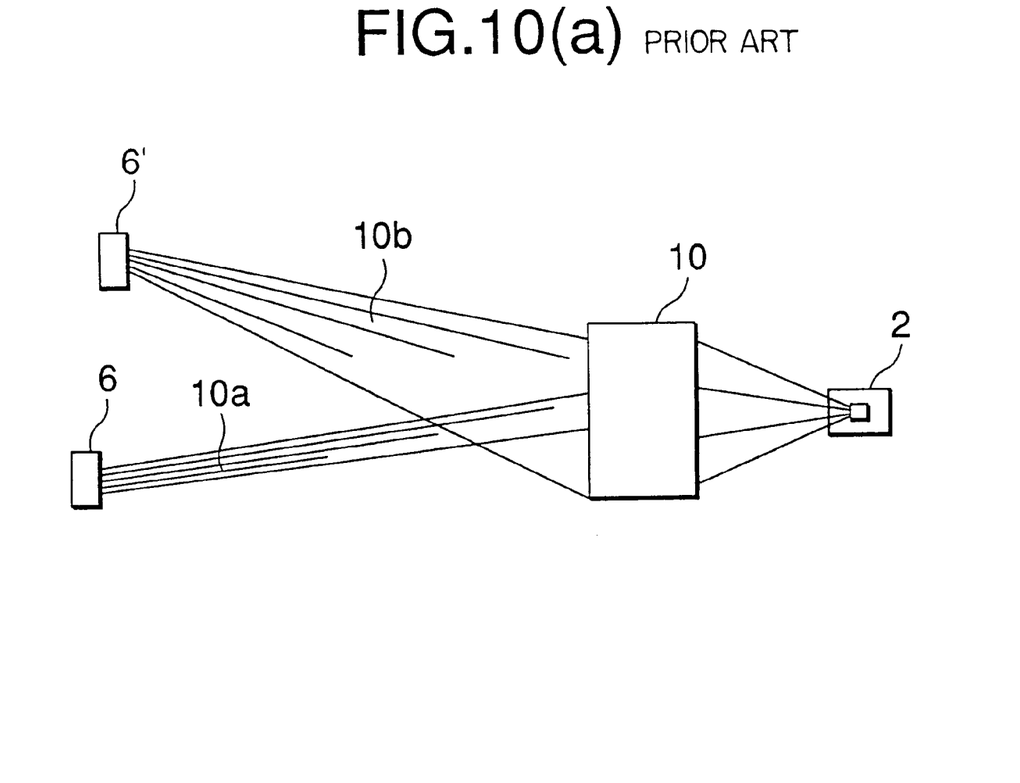
FIGS. 10(a) and 10(b) are views showing another example of the conventional art.
Figure 10B:
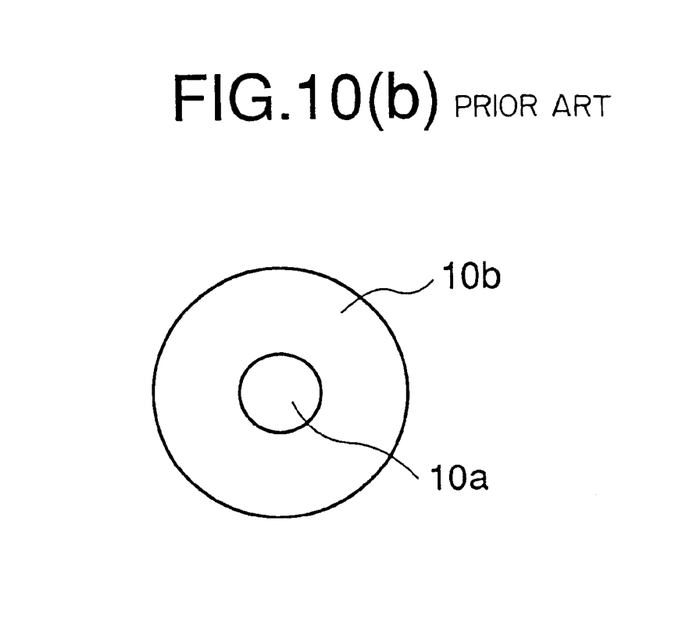

FIGS. 10(a)–10(b) shows another device described in Unexamined Japanese patent application HEI. 8-271509. In the device, light is not split into plural regions of different scattering angles, but split by using an optical fiber bundle 10. Namely, forward scatter emitted from particles in the flow cell 2 impinges on a light receiving face of the optical fiber bundle 10. In the light receiving face, as shown in FIG. 10(b), an optical fiber group 10a for receiving forward small angle scatter is disposed at the center, and an optical fiber group 10b for receiving forward large angle scatter is disposed in the periphery. As shown in FIG. 10(a), the emission side of the optical fiber group 10a is connected to the first detector 6, and that of the optical fiber group 10b to the second detector 6'. According to this configuration, scattering light entering the light receiving face of the optical fiber bundle 10 is supplied to either of the detectors 6 and 6' by a predetermined optical fiber group, in accordance with the scattering angle. In the same manner as the device of FIG. 8, the outputs of the first and second detectors 6 and 6' are supplied to the analyzer and then undergo a predetermined signal process.

However, the above-mentioned devices of the prior art have the following problems. In the device shown in FIG. 8, the optical for enabling the detectors 6 and 6' to receive light requires the collimator lens 3, the perforated mirror 4, and the collecting lenses 5. Therefore, the number of parts is increased, and the adjustment of the optical system is complicated and cumbersome. Furthermore, the optical system occupies a large area, and hence miniaturization of the whole of the device is impeded. In a device such as shown in FIG. 9 in which the number of split regions is increased and orthogonal scatters and back scatters are to be further detected, perforated mirrors, the number of which is equal to (the division number −1), and collecting lens the number of which is equal to the division numbers, are required. This causes the number of parts to be further increased, with the result that the above-mentioned problems become more serious.

In the device shown in FIGS. 10(a)–10(b), the collimator lens and the collecting lenses are not required, and the optical system requires only the optical fiber bundle. Even when the number of split regions is increased, it is necessary to increase only the number of optical fiber bundles. Unlike the device of FIGS. 8 and 9, the increase of the part number, and that of the occupied area are not large. However, the light receiving faces of optical fiber bundles must be concentrically arranged, and optical fibers must be collected in the unit of bundle. Therefore, a cumbersome process of routing optical fibers must be conducted. This causes the division number to be limited. Furthermore, the use of optical fibers brings a large loss. Specifically, a loss is produced when light passes through optical fibers, and light impinging on a clad is not transmitted. As a result, 50% or less of light impinging on the light receiving face of optical fiber bundle 10 shown in FIG. 10(a) can finally reach the detectors, thereby lowering the use efficiency of light.

SUMMARY OF THE INVENTION

The invention has been conducted in view of the above-mentioned circumstances. It is an object of the invention to provide a particle analyzer which can solve the problems discussed above, in which light can be split into plural regions of different scattering angles by a simple configuration, an optical system can be easily adjusted, and the use efficiency of light is high, in which, even when the number of split regions is increased, the number of parts of an optical system for splitting light is not increased so that the occupied area is not increased, and only an increase of the space due to an increased number of detectors is required, and in which the posture of a composite lens constituting the main portion of the invention can be performed easily and correctly so as to attain high measurement accuracy.

In order to attain the object, the particle analyzer of the invention is a particle analyzer in which particles are sorted by separately detecting regions of forward scatter which is produced by irradiating the particles with light, the regions having different scattering angles, and configured so that the particle analyzer comprises: a composite lens which is placed so as to block a light pathway of the forward scatter, and in which plural ring-like lens elements of different focal positions are integrally joined together in a state in which the lens elements are concentrically positioned, and a positioning element is optionally disposed in a center area; plural detectors for different scattering angles (in an embodiment, second and third detectors 17 and 18), the detectors being respectively placed at imaging positions of the forward scatter, the imaging positions respectively corresponding to the focal positions of the plural lens elements; a positioning detector (in the embodiment, a first detector 16) which can detect light which has passed through the positioning element; and analyzing means for sorting the particles on the basis of detection outputs of the plural detectors, and an optical axis of the positioning element coincides with at least a center of the composite lens, and, when the composite lens is perpendicular to the optical axis, the positioning element allows a predetermined amount of light to be received at a predetermined position of the positioning detector.

The imaging positions respectively corresponding to the focal positions where the detectors are disposed are not always coincident with the focal positions because of the following reason. The scatter impinging on the composite lens is not a parallel beam, and hence an image is not formed at the focal position. However, each of the imaging positions can be uniquely decided, because scattering occurs at a position of particles flowing through or dropping from the flow cell and the relative positional relationship between the flow cell and the composite lens is known.

According to this configuration, forward scatter impinges on a predetermined position of the composite lens. Specifically, forward small angle scatter having a small scattering angle impinges on a ring-like lens element which is positioned in a center area of the composite lens, and forward large angle scatter having a large scattering angle impinges on a lens element which is positioned in the periphery of the composite lens. Since the lens elements have different focal positions, the scatters impinging on the lens elements are formed into images at different positions, and then detected by the detectors, respectively.

In the invention, the positioning element is disposed at the center of the composite lens. Therefore, judgement on whether the posture of the composite lens attains a desired state or not can be easily performed by monitoring the output of the positioning detector. As a result, the positioning and the posture control can be easily performed.

The predetermined amount of light means an amount of light which is larger than a given reference. The given reference includes the following cases: when a pinhole is used as the positioning element, the given reference may be a predetermined value which is larger than 0; and, when a photodiode having a pinhole is used as the detector and a convex lens is used as the positioning element, for example, the reference value is 0 and it is judged whether the amount of light is larger than 0 or not (light is received or not).

Various elements may be used as the positioning element For example, a convex lens may be used, or a pinhole may be used.

The composite lens may be a conventional lens. When the composite lens is configured by a fresnel lens, the flow cytometer can be easily designed and produced, and the handling is facilitated. Therefore, this configuration is preferable.

The structure for attaining different focal points may be realized by various manners. For example, plural lens elements of different focal lengths may be joined together, plural lens elements of different principal axes may be joined together, or these structures may be combined with each other.

Boundary portions of the plural lens elements, and/or those of the periphery of the positioning element and the lens elements may be covered by annular masking members, respectively. When such portions are covered by masking members, light collection is performed on the basis of light passing through portions of the lens elements where the composition is stable. Consequently, noise components hardly enter the signals output from the detectors, and a measurement can be performed in a further accurate manner.

Furthermore, an obscurating member which blocks direct light emitted from a light source may be disposed at a predetermined position between a flow cell to which the particles are supplied, and the composite lens, and the obscurating member may be retractable when the composite lens is to be adjusted by using the positioning element. During a measurement, when direct light from the light source which is larger in amount and forward scatter impinge simultaneously on the detector, information of the forward scatter is canceled. To comply with this, usually, a flow cytometer is configured so that an obscurating member is disposed at a predetermined position so as to prevent direct light from impinging on a composite lens. When the posture of the composite lens is to be adjusted, the positioning element at the center of the composite lens must be irradiated with light. If such an obscurating member is disposed, however, it is impossible to irradiate the positioning element with light. Therefore the, obscurating member may be configured so as to be retractable, and, when the composite lens is to be adjusted, the obscurating member may be retracted so that the positioning element is irradiated with light, thereby allowing both the positioning and the measurement to be surely performed.

This retraction may be realized by, for example, a configuration in which the obscurating member is mounted on a slide-rail or the like and the member is moved along the slide-rail. In this case, the member may be coupled to driving means such as a motor so that the retraction is automatically performed. Alternatively, the obscurating member may be manually removed away from the disposition position. An example of such manual removal will be described. The obscurating member is detachably mounted on a holder for the composite lens. When the positioning is to be performed, the member is detached from the holder, and, when the measurement is to be performed, the member is attached to the holder.

In the invention, the positioning element is placed in the light pathway of direct light. When direct light spreads in a degree smaller than the positioning element, therefore, the lens elements are not irradiated with direct light and forward scatter. As a result, even when the intensity of direct light is high, the obscurating member is not always required.

DETAILED DESCRIPTION OF THE PREFERRED EMBODIMENTS

Hereinafter, embodiments in which the optical device of the invention is applied to a flow cytometer will be described.

Figure 1:
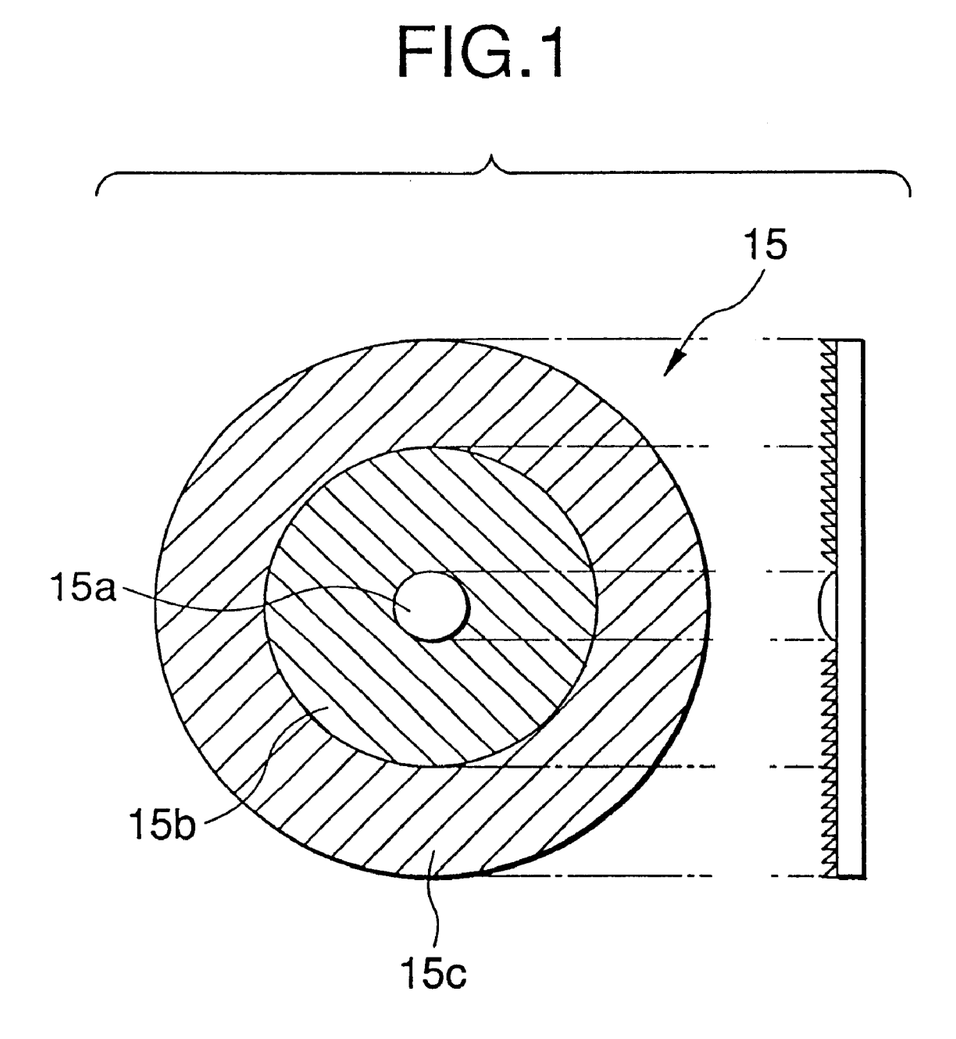
FIG. 1 is a view showing an example of a composite lens which is used in the invention.

FIG. 1 shows an example of a composite lens 15 which is used in an embodiment of the invention. As shown in the figure, in the example, a convex lens 15a serving as the positioning element is disposed at the center, and two or first and second ring-like lens elements 15b and 15c are integrally joined to each other in a state in which the lens elements are concentrically positioned in the periphery of the convex lens, thereby forming the composite lens 15.

In the example, each of the lens elements 15b and 15c is formed by cutting a fresnel lens into a suitable shape. The convex lens 15a and the lens elements 15b and 15c are fitted to one another and integrated by bonding the junction faces, thereby forming the single composite lens 15. The convex lens 15a and the first and second lens elements 15b and 15c have different focal positions. According to this configuration, light emitted from the same object is collected by each of the convex lens 15a and the first and second lens elements 15b and 15c so as to form images at different positions.

Figure 11:
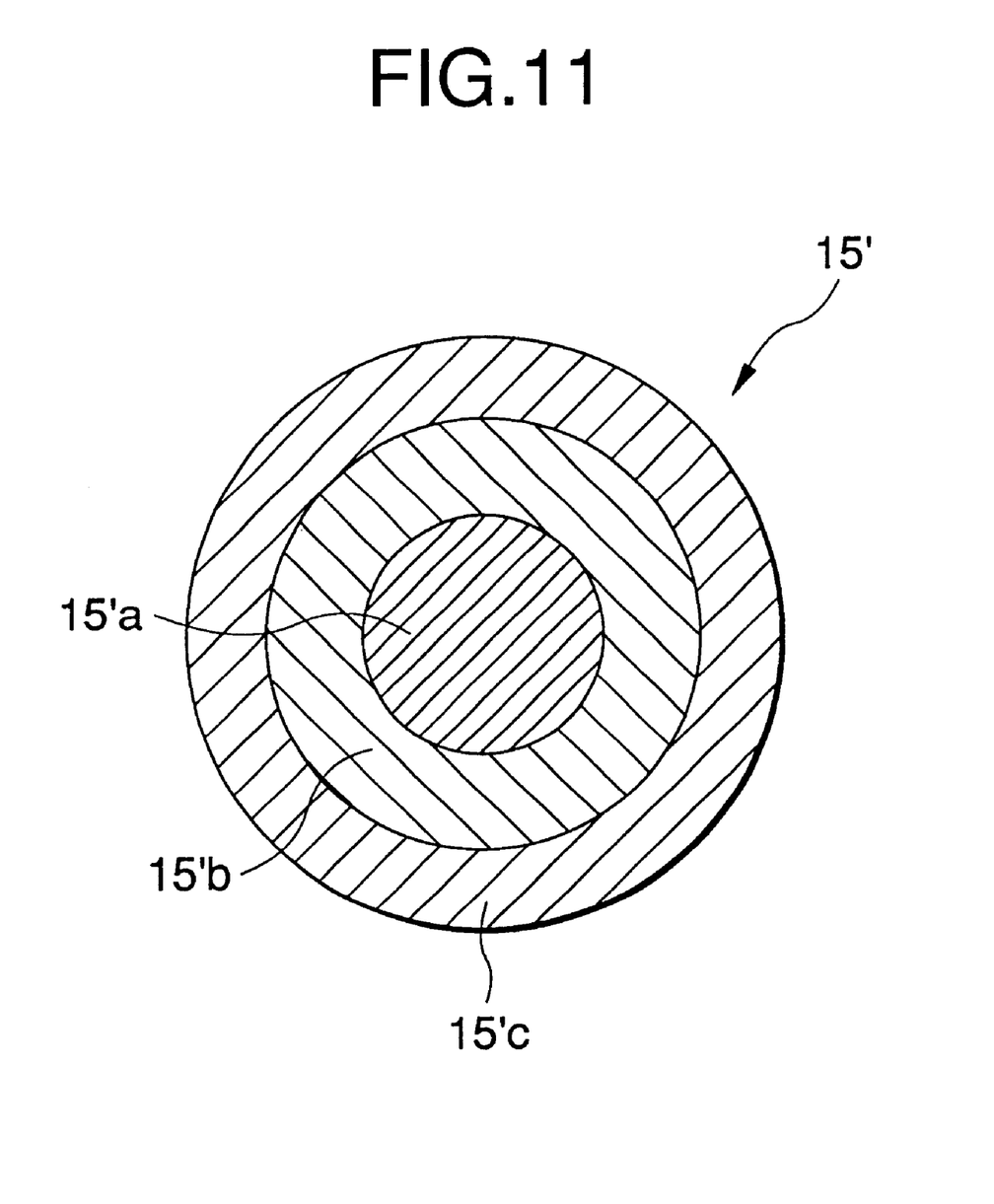
FIG. 11 is a view showing another example of a composite lens which is used in the invention.

The structure for forming different focal positions may be realized by using lens elements of different focal lengths as the lens elements 15a to 15c, or making the principal axes different from one another. FIG. 11 shows another example of a composite lens 15'; including convex lens 15' a and first and second lens elements 15'b and 15'c, which does not include the positioning element.

Figure 2:
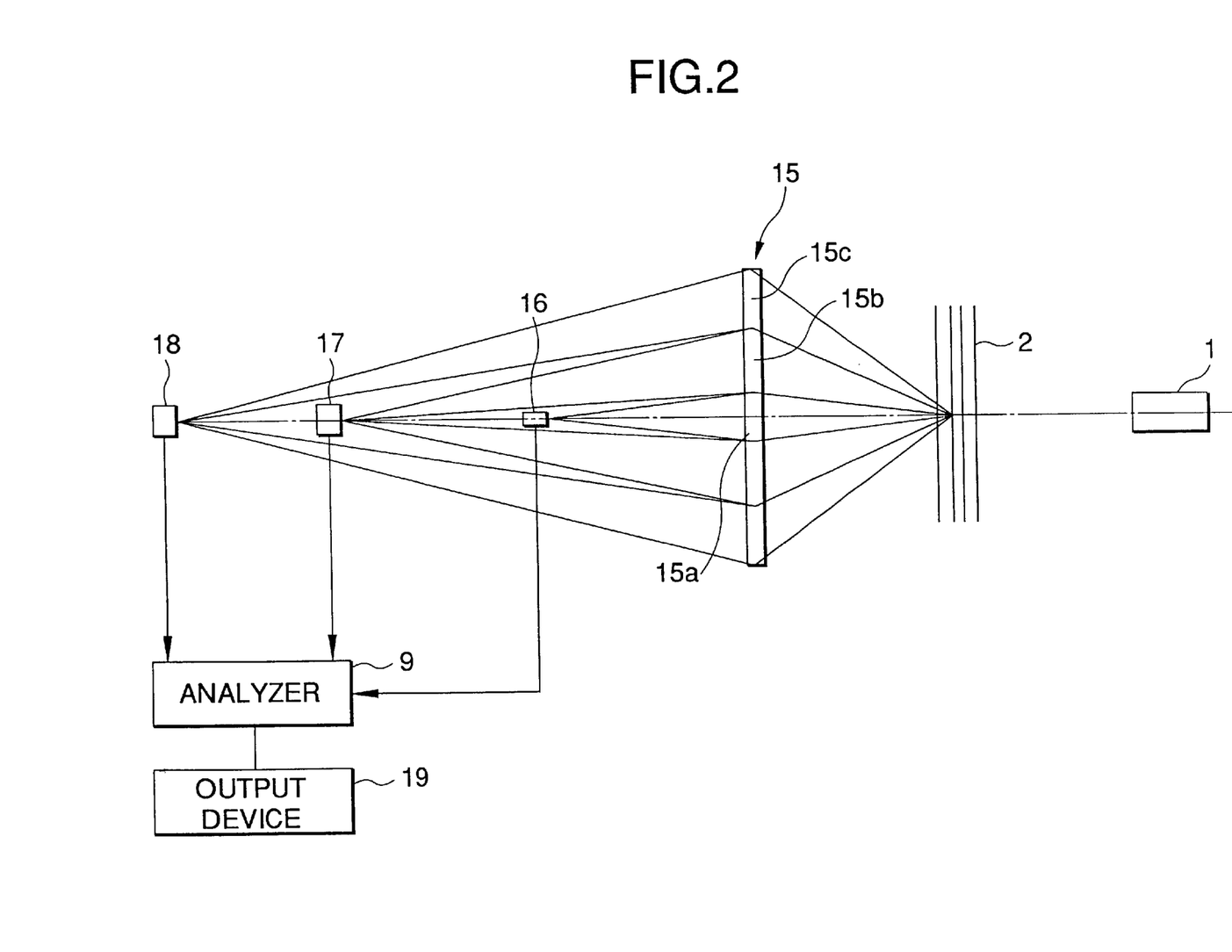
FIG. 2 is a view showing a first embodiment of the particle analyzer of the invention.

FIG. 2 shows an embodiment of the particle analyzer (the flow cytometer) of the invention which uses the above-mentioned composite lens with respect to the forward scatter. As shown in the figure, a flow cell 2 and the composite lens 15 are arranged in this sequence in the pathway of light emitted from a laser light source 1. Although not illustrated, a collecting lens is disposed on the emission side of the laser light source 1 so that light is converged at the position where the flow cell 2 is disposed. When particles in the flow cell 2 are irradiated with laser light, forward scatter is produced. The center (optical axis) of the traveling path of the forward scatter coincides with that of the composite lens 15. The composite lens 15 is placed so that the composite lens 15 is perpendicular to the optical axis.

Among the elements 15a to 15c constituting the composite lens 15, the convex lens 15a at the center has the shortest focal length, and the second lens element 15c in the outermost periphery has the longest focal length. However, the principal axes of the elements 15a to 15c coincide with one another. According to this configuration, light emitted from the same object passes through each of the elements 15a to 15c so as to be collected, but images are formed at different positions. Specifically, all the images are formed on the center line (optical axis) of the composite lens 15, but the image forming position of the convex lens 15a is closest to the composite lens 15 and that of the second lens element 15c is remotest from the composite lens 15.

A first detector 16, a second detector 17, and a third detector 18 are arranged in this sequence in front of the composite lens 15. The centers of the detectors 16 to 18 and the center of the composite lens 15 are positioned on the same line. In other words, the detectors 16 to 18 are arranged so that the optical axes of the light receiving faces of the detectors coincide with the center axis of the light pathway of the light emitted from the laser light source 1. The first detector 16 is placed at the image forming position of light which has passed through the convex lens 15a of the shortest focal length, the second detector 17 at the image forming position of light which has passed through the first lens element 15b of the medium focal length, and the third detector 18 at the image forming position of light which has passed through the second lens element 15c of the longest focal length.

Each of the detectors 16 to 18 is configured by a photodiode (PD) or another light/voltage converter element. The outputs of the detectors 16 to 18 are supplied to an analyzer 9 which analyzes the particles. In the first detector 16, a pinhole is formed so as to coincide with the center of the light receiving face, thereby preventing light deviated from the center from being detected. The analysis result based on the outputs of the second and third detectors 17 and 18 is supplied to an output device 19. The analyzing and sorting process on the basis of signals of different scattering angles can be performed in the same manner as the conventional art, and hence its detailed description is omitted.

Next, the procedure of the measurement using the flow cytometer will be described. The measurement includes a positioning process in which the posture of the composite lens 15 is adjusted to the measurement, and an actual analyzing and sorting process which is performed after the positioning process. The positioning process may be performed for each measurement. Alternatively, the adjustment may be performed regularly or irregularly for every several measurements.

Positioning Process

The positioning process is performed in a state in which no sample which causes scattering is supplied to the flow cell 2. Since there is no scattering source, laser light emitted from the laser light source 1 passes through the flow cell 2 as it is, and most of the light impinges on the convex lens 15a which serves as the positioning element, at the center of the composite lens 15, so as to form an image at a predetermined position. When the composite lens 15 is positioned with being longitudinally deviated with respect to the flow cell 2 and the laser light source 1, the image formation is not performed in the light receiving face of the first detector 16. Even in the case where the composite lens is correctly positioned in the longitudinal direction, when light fails to impinge on the center of the composite lens 15 (the convex lens 15a), an image is formed at a position where the first detector 16 is disposed, but the image forming position is deviated from the center of the light receiving face of the first detector 16 in accordance with the direction and degree of the deviation of the composite lens 15. In the embodiment, the pinhole is formed in front of the light receiving face of the first detector 16 and only light the direction of which coincides with the center axis can pass through the pinhole. Therefore, light which is positionally deviated as described above cannot pass through the pinhole and does not reach the light receiving face of the first detector 16. Similarly, even in the case where light impinges on the center of the composite lens 15 (the convex lens 15a), when the composite lens 15 is inclined, the light obliquely impinges on the center of the convex lens 15a to be refracted thereby, with the result that an image is formed at a position deviated from the center of the light receiving face of the first detector 16. In this way, such light is blocked by the pinhole so as not to impinge on the light receiving face of the first detector 16.

Therefore, when the composite lens 15 is disposed so that the center of the lens is on the optical axis, the lens is perpendicular to the optical axis, and the positional relationships in the longitudinal direction satisfy a desired state, light which passes through the convex lens 15a to form an image impinges on the light receiving face of the first detector 16. As a result, the posture of the composite lens 15 can be adjusted while monitoring the output of the first detector 16. When the output of the first detector 16 is ON (light is received), this means that the composite lens 15 is disposed in a correct state. Consequently, the posture of the composite lens 15 is held in the state, and the positioning process is then ended.

For the sake of illustration, the convex lens 15a is shown so as to have a relatively large diameter. In the positioning process, it is required only to judge whether light forms an image on the center axis of the first detector or not. Therefore, the convex lens 15a may have a smaller diameter. In the actual measurement which will be described later, light impinging on the convex lens 15a is not used except when the absorbance of the sample is measured. Consequently, it is preferable to set the diameter of the convex lens 15a to be as small as possible, also from the view point of efficient use of light in the measurement.

Actually, since the composite lens 15 is fixed to a holder or the like which is disposed at a predetermined position in the flow cytometer, the position and posture of the composite lens are approximately correct. Occasionally, the positioning in at least one direction (for example, in the longitudinal direction with respect to the optical axis) is already attained. In such a case, the adjustment is performed in the remaining directions.

In the embodiment described above, a photodiode having a pinhole is used as the first detector 16. The invention is not restricted to this. For example, it may be judged whether an image is formed at the center of the light receiving face or not, by using a position sensitive detector (PSD) or the like.

In the embodiment, since the positioning can be performed without supplying a sample, description has been made in the case where no sample is supplied. It is a matter of course that the positioning may be performed with supplying a sample. When the above-described method is employed, scattering does not occur and hence a larger number of kinds of light can be used for positioning. Therefore, this method is preferable.

Analyzing and Sorting Process

The analyzing process is performed by using the outputs of the second and third detectors 17 and 18. As seen from FIG. 2 also, forward small angle scatter having a small scattering angle (for example, 1.5 to 10 deg.) impinges on the first lens element 15b to be collected thereby, and is then received by the second detector 17 which is the second one counted from the composite lens 15.

Forward large angle scatter having a large scattering angle (for example, 10 to 15 deg.) impinges on the second lens element 15c in the outermost periphery to be collected thereby, and is then received by the third detector 18 which is remotest from the composite lens 15.

In this way, plural regions of different scattering angles can be separately collected by the single composite lens 15. In other words, the optical system, which is configured in the conventional art by a perforated mirror, a collimator lens, or plural collecting lenses, can be configured by the single composite lens. Therefore, the configuration is simplified, the occupied area is reduced, and the adjustment is easily performed. Even when the number of split regions is increased, it is required only to increase the number of lens elements and hence the size is not enlarged. Since the collection of light is performed by using only the lens, a substantially whole of forward scatter can impinge on the detectors.

Therefore, the use efficiency of light is so high that even light of a minute level can be surely detected.

Figure 3:
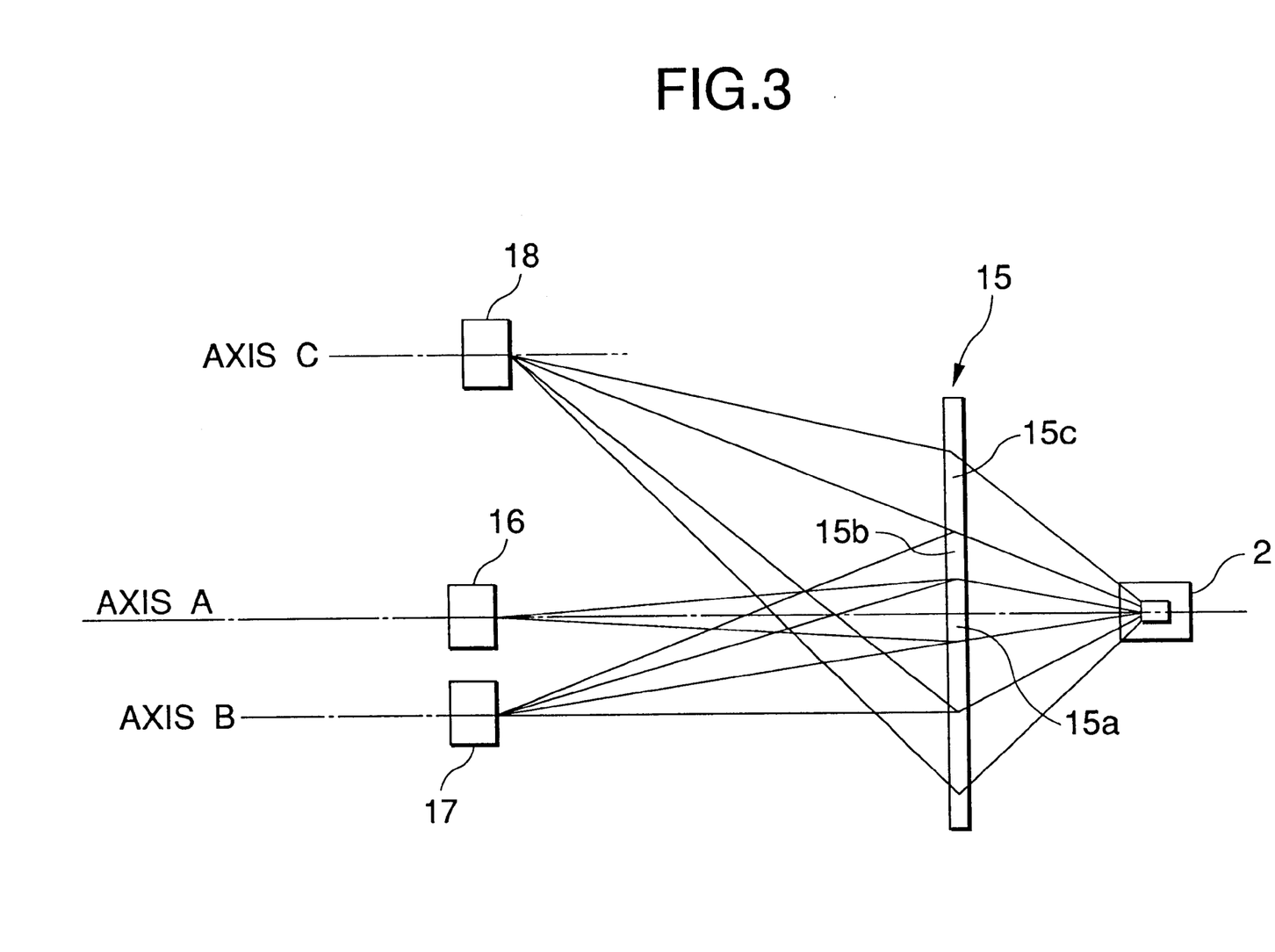
FIG. 3 is a view showing a second embodiment of the particle analyzer of the invention.

FIG. 3 shows a second embodiment of the invention in case of the forward scatter. Unlike the first embodiment described above, the elements 15a to 15c of the embodiment have different principal axes. According to this configuration, light which has passed through the elements 15a to 15c to be collected forms an image at a predetermined position of each of the principal axes, and hence can be split into plural regions of different scattering angles.

In this case also, the center of the composite lens 15 is the convex lens 15a serving as the positioning element, the principal axis A coincides with the optical axis of light emitted from the laser light source 1, and the first detector 16 is disposed on an extension line of the axis.

Furthermore, forward small angle scatter having a small scattering angle impinges on the first lens element 15b to be collected thereby, and is then received by the second detector 17 placed at a predetermined position which is deviated from the principal axis A in the downward direction in the figure and which is on the principal axis B. Forward large angle scatter having a large scattering angle impinges on the second lens element 15c in the outermost periphery to be collected thereby, and is then received by the third detector 18 placed at a predetermined position which is deviated from the principal axis A in the upward direction in the figure and which is on the principal axis C.

Although not illustrated, the outputs of the detectors 16 to 18 are supplied to the analyzer in the same manner as FIG. 2. The positioning of composite lens 15 is performed on the basis of the output of the detector 16, and particles in the flow cell 2 are analyzed and sorted on the basis of the outputs of the second and third detectors 17 and 18.

In the example described above, the elements 15a to 15c have the same focal length. As shown in FIG. 3, therefore, the detectors 16 to 18 are disposed at the positions which are separated from the composite lens 15 by the equal distance. The invention is not restricted to this. It is a matter of course that the elements may have different focal lengths. The other configuration and effects are the same as those of the first embodiment and hence their detailed description is omitted.

Figure 4:
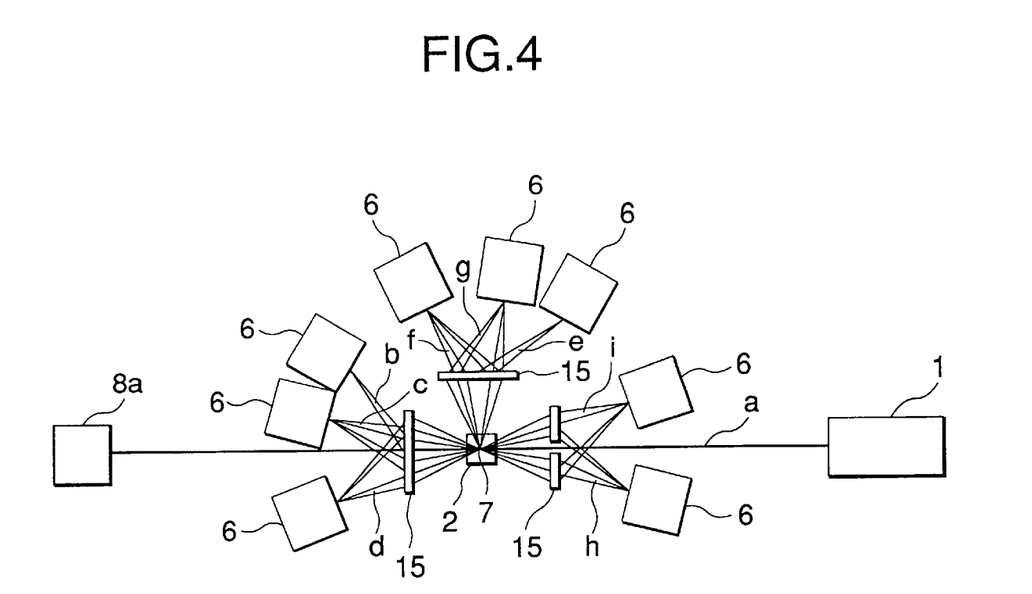
FIG. 4 is a view showing a third embodiment of the particle analyzer of the present invention.

FIG. 4 shows an embodiment in which the invention is applied to a flow cytometer which uses orthogonal scatters and back scatters in addition to forward scatters. Referring to the figure, the embodiment is structured in the following manner. Irradiation light a emitted from the laser light source 1 passes through the center portion of the composite lens for separating back scatters and then impinges on the particles 7 serving as the scattering source of the flow cell 2, thereby obtaining forward scatters b, c, and d, orthogonal scatters e, f, and g, and back scatters h and i. The scatters are sorted by composite lenses 15 which are respectively disposed in the directions of the scatters, and the light intensities are detected by the respective detectors 6. The direct light from the laser light source 1 which has passed through the flow cell 2 is detected by a detector 6a which is used for positioning. The embodiment is an example in which the composite lens 15 of the invention is applied to the prior art example of a flow cytometer shown in FIG. 9. In the prior art example, as the number of scatters to be detected is increased, the number of the optical systems 8 each consisting of the collimator lens 3, the mirror 4, and the collecting lenses 5 is increased to cause miniaturization of the device to be impeded. By contrast, when the composite lens 15 of the invention is used, each of the optical systems 8 can be replaced with a single composite lens, with the result that a flow cytometer which is small in size and economical can be provided. In the prior art, each of the optical axes of the collimator lens 3, the mirror 4, and the collecting lens 5 must be adjusted. In contrast, the embodiment has a merit that it is required only to adjust the composite lens 15 and hence the measurement using the device can be performed very easily. When the composite lens is produced by using molds, dispersion of focal positions of the lens elements in one composite lens can be intrinsically eliminated.

Figure 5:
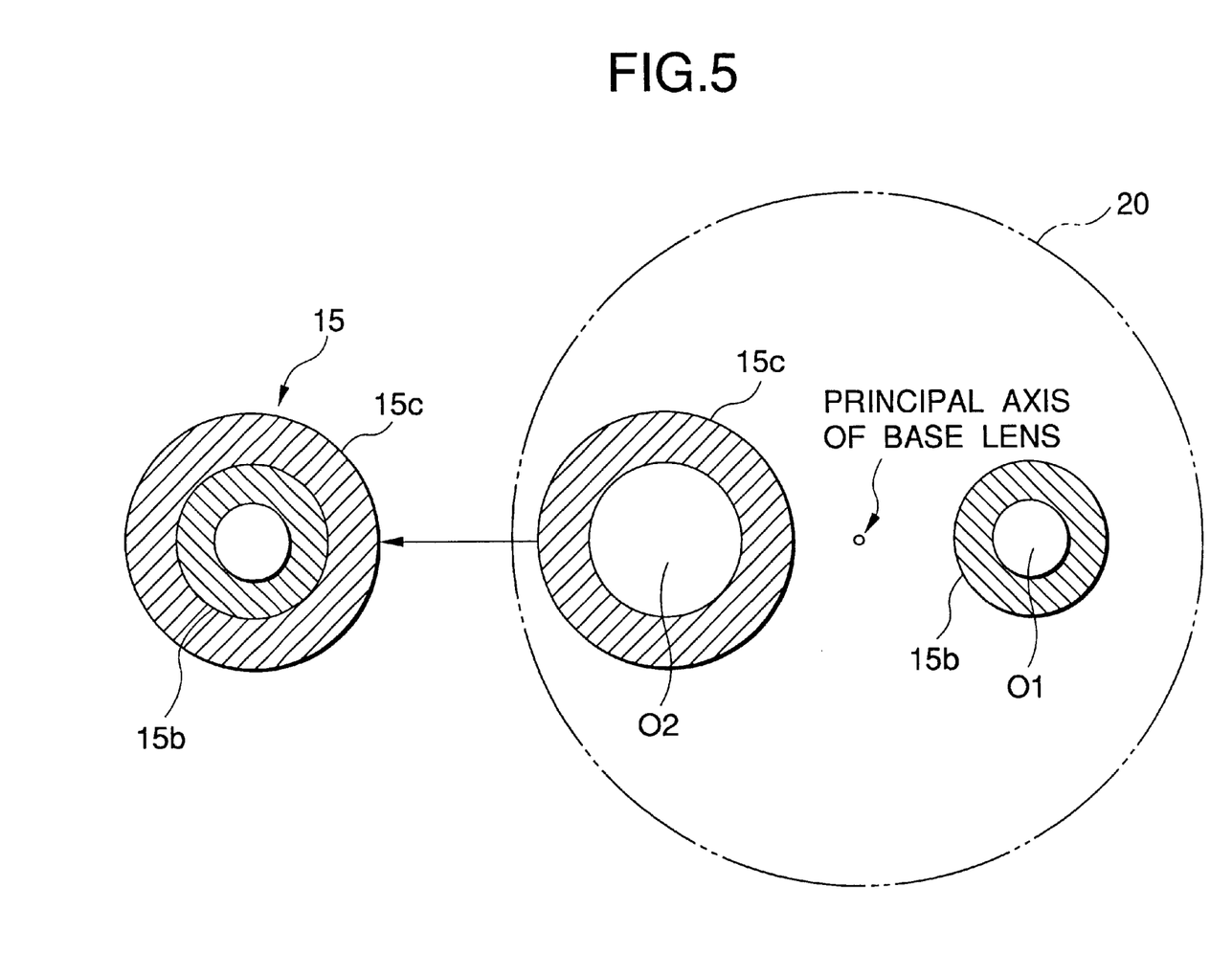
FIG. 5 is a view showing an example of the method of producing the composite lens.

FIG. 5 shows an example of the method of producing the composite lens 15 used in the second embodiment described above. In the second embodiment, the first and second lens elements 15b and 15c have the same focal length and are different only in principal axis from each other. Consequently, a base lens 20 which is configured by a large fresnel lens is prepared as shown by the two-dot chain line in the figure. The first lens element 15b is formed by cutting out a ring-like portion of a medium diameter at a position which is separated from the principal axis of the base lens 20 by a predetermined distance. The principal axis of the first lens element 15b coincides with that of the base lens 20, and hence is deviated from the center $O_1$, of the ring in the leftward direction in the figure. The second lens element 15c is formed by cutting out a ring-like portion of a large diameter at a position which is in the side opposite to the first lens element 15b and which is separated from the principal axis of the base lens 20 by a predetermined distance. The principal axis of the second lens element 15c coincides with that of the base lens 20, and hence is deviated from the center $O_2$ of the ring in the rightward direction in the figure. As a result, the principal axes of the first and second lens elements 15b and 15c are separated by a predetermined distance from the respective centers, and the deviation directions of the elements 15b and 15c are opposite to each other. In this way, plural lens elements can be produced by cutting out portions at appropriate positions of a single large fresnel lens. The composite lens can be easily produced by joining these lens elements together. As the number of lens elements to be joined to one another is larger, the production process is more effective in the production of lens elements of the same focal length. It is a matter of course that the lens elements are not required to be produced from a single fresnel lens.

The lenses are used for the purpose of exhibiting a function of focusing light impinging on regions having a predetermined area, in the respective regions. Therefore, each of the lenses can be produced in the following manner. First, plural lenses, such as fresnel lenses, having a focal length which conforms to the design of the device are prepared. Plural lens elements are cut or gouged out from the lenses so as to have a predetermined shape and area.

The lens elements are joined together integrally and flatly to form each of the lens. The plural prepared lenses may have different focal lengths. The principal axes of the lens elements may be designed so as to coincide with each other. Alternatively, the principal axes may be designed so as to be different from each other. As a result of such a shaping process, an optical system unit may be compactly produced in a limited space.

Figure 6A:
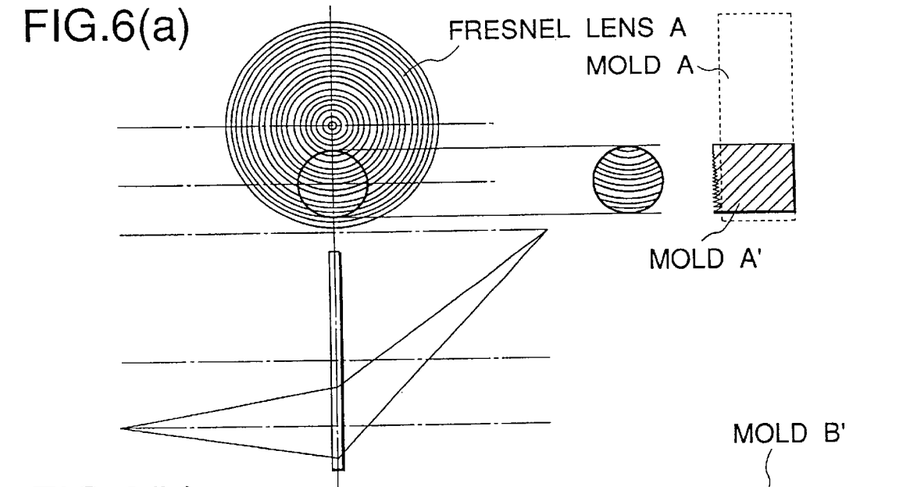
FIGS. 6(a)–6(c) are views showing another example of the method of producing the composite lens.
Figure 6B:
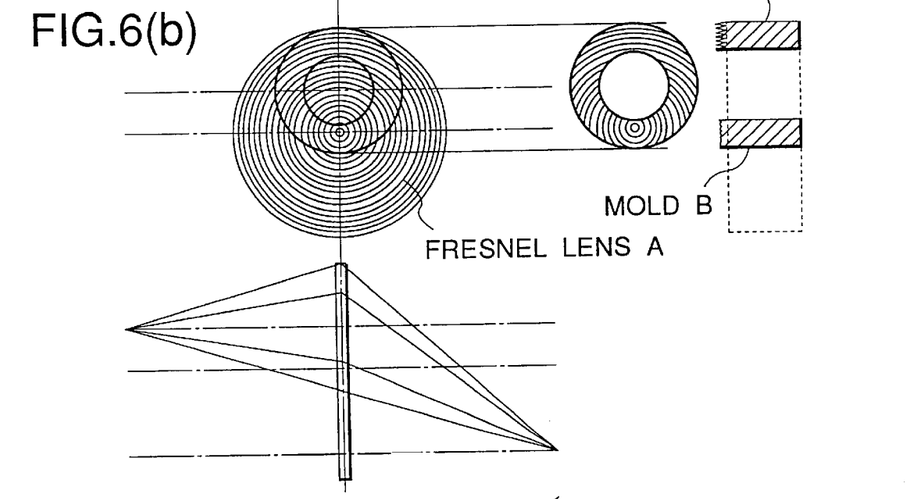
Figure 6C:
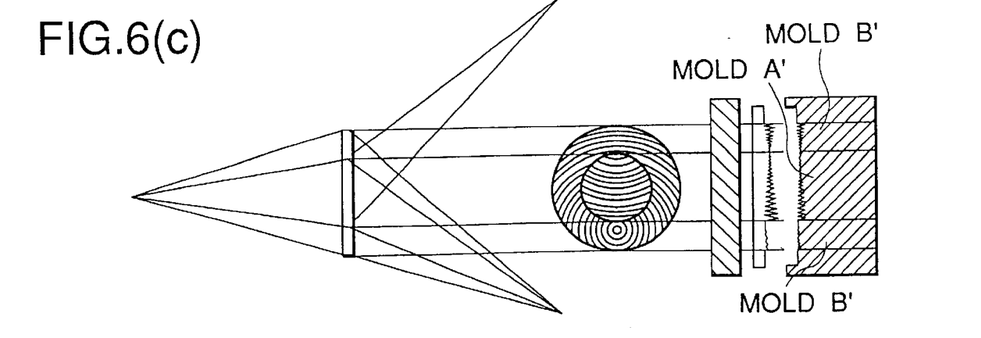

The composite lens 15 may be produced by, in place of the above-described method, producing molds respectively having surfaces which correspond to the lens elements, or a mold having a surface in which the lens elements are combined with one another, and performing a technique such as the compression mold, the ICM (Injection Compression Mold), or the injection mold, with using the mold (s). FIGS. 6(a)–6(c) shows an example of the production. A mold A' is formed by cutting or gouging out a circular shape from a mold A from which a fresnel lens A can be shaped. An annular mold B' having a hole into which the mold A' can be incorporated is formed by cutting or gouging out it from a mold B from which a fresnel lens B can be shaped. Then the mold A' is incorporated into the mold B', with the result that the mold surface can be shaped. The molds A' and B' may form the same fresnel lens. Alternatively, the molds may form fresnel lenses of different focal lengths or different principal axes, respectively.

Figure 7:
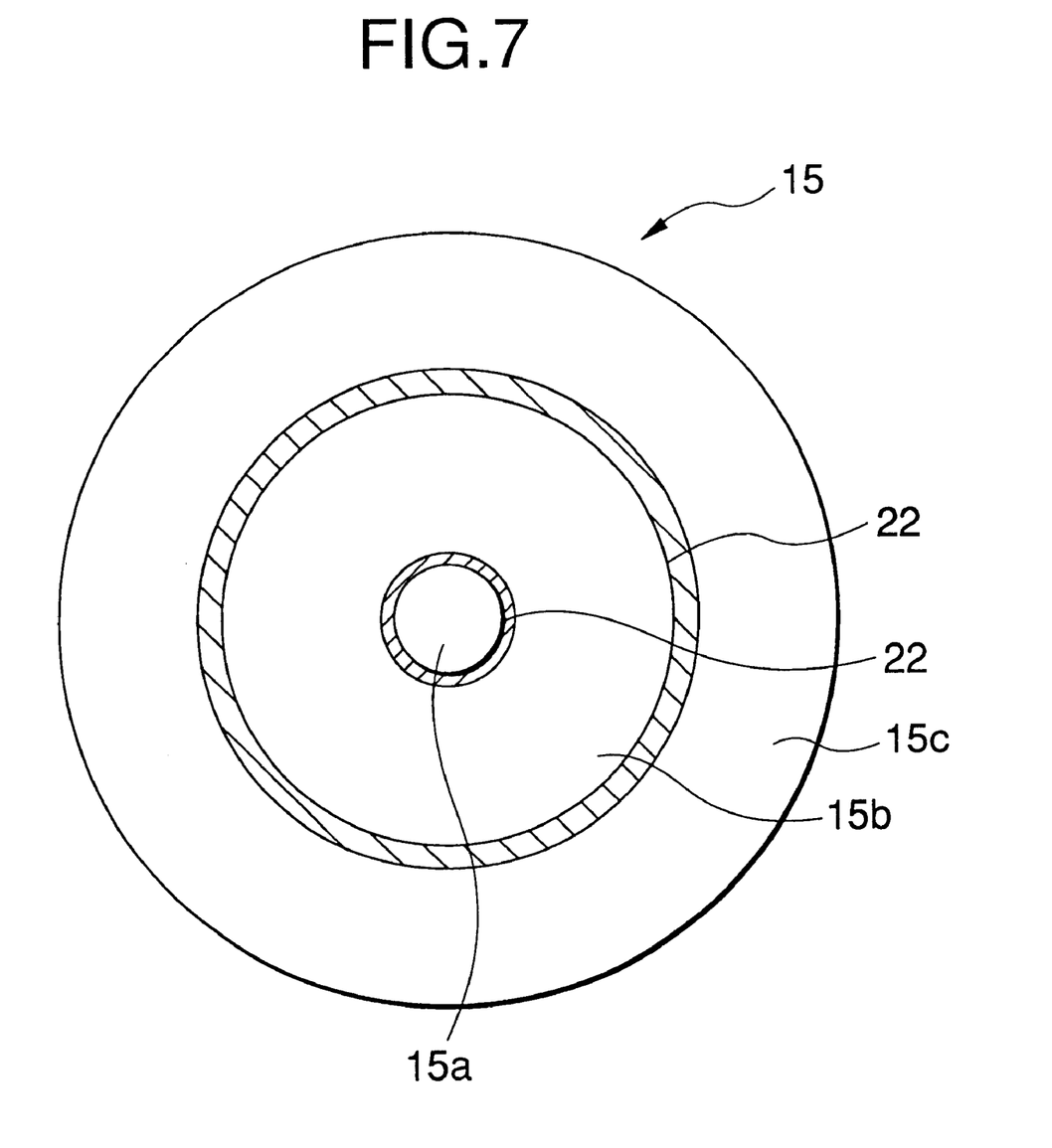
FIG. 7 is a view showing another example of the composite lens which is used in the invention.

FIG. 7 shows another embodiment of the invention in which the composite lens 15 has a further improved configuration. In the embodiment also, two regions, i.e., the first and second lens elements 15b and 15c are separately detected. The junction area between the adjacent lens elements, and that between the convex lens 15a and the first lens element 15b are covered by ring-like masking members 22, respectively. After the elements 15a to 15c are joined together, a material which is optically opaque is attached to each of the junction portions, thereby forming the masking members 22. Specifically, such a member is realized by forming a given thin film by evaporating or sputtering and then patterning the thin film, by applying predetermined ink or the like, or by pasting a tape member or the like.

When the masking members 22 are not disposed, there is a fear that light is irregularly reflected by the junction portions and fails to be correctly collected onto the predetermined detectors, thereby producing noise components. In contrast, in the embodiment, since the masking members 22 are disposed, light is caused to pass through only normal portions of the lens elements. Therefore, the detectors can receive light in a desired state. The composite lens 15 in which the masking members 22 are disposed can be applied to any one of the above-described embodiments.

Further when using a composite lens that does not include a positioning element shown in FIG. 11 or the like, positioning detectors (FIGS. 2 and 3), method of producing the composite lens (FIGS. 5 and 6(a) and 6(c), or disposing the masking members (FIG. 7) can be performed in the same manner as described above.

In the above-described embodiments, the convex lens 15a is used as the positioning element. The invention is not restricted to this. For example, a pinhole may be formed at the center of the composite lens 15, and the pinhole may be used as the positioning element.

When a pinhole is used, the following effects are attained. When the center of the composite lens 15 fails to coincide with the optical axis of light emitted from the laser light source 1, for example, the light cannot pass through the pinhole and does not reach the light receiving face of the first detector. When the composite lens 15 is inclined, the amount of light passing through the pinhole is reduced and the output level of the first detector 16 is lowered. When the inclination angle is made larger, light cannot pass through the pinhole. Consequently, the posture control of the composite lens 15 can be performed by monitoring the output of the first detector. Specifically, when the amount of light becomes higher than a given level, or when the amount of light becomes maximum, it is possible to judge that the positioning is attained. However, the configuration using such a pinhole cannot cope with longitudinal positional deviation in the direction of the optical axis. When the positioning in the longitudinal direction is not required, therefore, there is an advantage that the positioning element can be formed by a simple configuration in which a pinhole is formed at the center of the composite lens.

In all the embodiments described above, the composite lens is configured by combining two lens elements with each other. Alternatively, three or more lens elements may be used. In each of the embodiments, the lens elements or the composite lens is configured by using a fresnel lens. The invention is not restricted to this. The lens elements or the composite lens may be configured by using a conventional lens such as a convex lens.

Of course, it is applicable for employing the composite lens 15' without the positioning element as shown in FIG. 11.

Although not illustrated, the embodiments may be configured in the following manner. An obscrulator (having the same function as the one indicated by 11 in FIG. 8) serving as the obscurating member is disposed at a predetermined position between the flow cell and the composite lens, and direct light emitted from the laser light source 1 is blocked by the obscrulator. In this case, the obscrulator is movably disposed. When a usual measurement is to be performed, the obscrulator is positioned in the light pathway of the direct light. When the posture of the composite lens is to be adjusted, the obsculate is retracted from the light pathway so that direct light emitted from the laser light source 1 enters the positioning element 15a. The obscurating member is not restricted to a member used in the conventional art, such as an obscrulator, and may be a member which is directly or indirectly attached to the composite lens 15. The obscurating member may have any structure.

In contrast to the embodiment described above, an embodiment may be configured so that direct light is not blocked by the obsculator also during an actual measurement which is performed after the posture control of the composite lens, the collecting lens is disposed at an appropriate position between the flow cell and the composite lens, and the output of the first detector 16 is detected. In the embodiment, it is possible to measure the absorbance of particles flowing through the flow cell.

As described above, according to the particle analyzer of the invention, plural lens elements of different focal positions are integrally joined together to produce a single composite lens, regions of light of different scattering angles are split by the composite lens, and the split regions are distributed to detectors.

Furthermore, this can be performed by a single member or the single composite lens. Therefore, the reduction of the number of parts, and the adjustment of the optical system can be easily performed. Since the collection of light is done only by the lens, the use efficiency of light is high. Even when the number of split regions is increased, only an increase of the number of the lens elements is required, and only the single composite lens is necessary as a part. The number of parts of the optical system of splitting light is not increased. Therefore, the occupied area is not increased, and only an increase of the space due to an increased number of detectors is required.

The positioning element such as a convex lens or a pinhole is disposed at the center of the composite lens. When it is judged when light normally passes through the positioning element or not, therefore, it is possible to judge whether the position and posture of the composite lens are correct or not. Consequently, the positioning process can be performed easily and correctly.

While the present invention shall now be described with the reference to the preferred embodiments shown in the drawings, it should be understood that the intention is not to limit the invention only to the particular embodiments shown but rather to cover all alterations, modifications and equivalent arrangements possible within the scope of appended claims.

What is claimed is:

1. A mold for shaping a composite lens comprising:
   plural lens surfaces of different focal axes are annularly arranged in a molding face, wherein said mold comprises two separate sections taken from non-concentric portions of an existing lens mold, said sections disposed in a concentric manner to form said mold.

2. A mold for shaping a composite lens comprising:

plural lens surfaces of different focal axes are annularly arranged in a molding face, wherein said mold is shaped so that a first section of said mold represents a shape of a first corresponding section of an existing lens mold, and a second section of said mold represents a shape of a second corresponding section of said existing lens mold, said first and second sections of said mold being concentric with respect to each other and said first and second corresponding sections of said existing lens mold being non-concentric with respect to each other.

3. A mold for shaping a composite lens according to claim 1, wherein said sections each have a center, and said sections are taken from locations in said existing lens mold where the centers of said sections are equidistant from the center of said existing lens mold.

4. A mold for shaping a composite lens according to claim 2, wherein said corresponding sections of said existing lens mold each have a center, and said corresponding sections of said existing lens mold are located in said existing lens mold such that the centers of said corresponding sections are equidistant from the center of said existing lens mold.

5. A mold according to claim 1, further comprising more than two concentric sections.

6. A mold according to claim 2, further comprising more than two concentric sections of said mold.

7. A mold for shaping a composite lens comprising:

plural lens surfaces of different focal axes are annularly arranged in a molding face, wherein said mold comprises two separate sections taken from multiple existing lens molds, said sections disposed in a concentric manner to form said mold.

8. A mold for shaping a composite lens comprising:

plural lens surfaces of different focal axes are annularly arranged in a molding face, wherein said mold is shaped so that a first section of said mold represents a shape of a first corresponding section of a first existing lens mold, and a second section of said mold represents a shape of a second corresponding section of a second existing lens mold, said first and second sections of said mold being concentric with respect to each other.

* * * * *